US010537295B2

(12) United States Patent
Watanabe et al.

(10) Patent No.: US 10,537,295 B2
(45) Date of Patent: Jan. 21, 2020

(54) RADIATION IMAGING APPARATUS AND RADIATION IMAGING SYSTEM

(71) Applicant: CANON KABUSHIKI KAISHA, Tokyo (JP)

(72) Inventors: Minoru Watanabe, Yokohama (JP); Keigo Yokoyama, Kawasaki (JP); Masato Ofuji, Takasaki (JP); Jun Kawanabe, Kawasaki (JP); Kentaro Fujiyoshi, Tokyo (JP); Hiroshi Wayama, Kawasaki (JP); Kazuya Furumoto, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 182 days.

(21) Appl. No.: 15/556,714

(22) PCT Filed: Mar. 31, 2016

(86) PCT No.: PCT/JP2016/001867
§ 371 (c)(1),
(2) Date: Sep. 8, 2017

(87) PCT Pub. No.: WO2016/189788
PCT Pub. Date: Dec. 1, 2016

(65) Prior Publication Data
US 2018/0055464 A1    Mar. 1, 2018

(30) Foreign Application Priority Data
May 22, 2015    (JP) .................................. 2015-104912

(51) Int. Cl.
*A61B 6/00*      (2006.01)
*H01L 31/0232*   (2014.01)
(Continued)

(52) U.S. Cl.
CPC ............ *A61B 6/4233* (2013.01); *A61B 6/542* (2013.01); *H01L 27/14605* (2013.01);
(Continued)

(58) Field of Classification Search
CPC . A61B 6/4233; A61B 6/542; H01L 27/14605; H01L 27/14663;
(Continued)

(56) References Cited

U.S. PATENT DOCUMENTS 6,034,406 A * 3/2000 Kobayashi ........ H01L 27/14603
257/435
7,381,963 B2   6/2008 Endo et al.
(Continued)

FOREIGN PATENT DOCUMENTS

CN    101682687 A    3/2010
CN    102315233 A    1/2012
(Continued)

OTHER PUBLICATIONS

U.S. Appl. No. 15/631,205, Hiroshi Wayama, filed Jun. 23, 2017.
U.S. Appl. No. 15/543,415, Kentaro Fujiyoshi, filed Jul. 13, 2017.

*Primary Examiner* — Michael C Bryant
(74) *Attorney, Agent, or Firm* — Venable LLP

(57) ABSTRACT

A radiation imaging apparatus is provided. The apparatus comprises pixels arranged in an image sensing region, a first and a second detecting elements configured to obtain radiation irradiation information, a first signal line to which a signal from the first detecting element is to be output and a second signal line to which a signal from the second detecting element is to be output, and a signal processing circuit configured to process the signals output from the first and the second detecting elements. The first the second signal lines are arranged in the image sensing region or arranged adjacent to the image sensing region, the first (Continued)

detecting element has a larger region to detect radiation than the second detecting element. The signal processing circuit generates the radiation irradiation information based on the signals from the first and the second signal lines.

28 Claims, 13 Drawing Sheets

(51) Int. Cl.
  *H04N 5/361* (2011.01)
  *H04N 5/32* (2006.01)
  *H01L 27/146* (2006.01)
  *G01T 1/20* (2006.01)

(52) U.S. Cl.
  CPC .. *H01L 27/14609* (2013.01); *H01L 27/14623* (2013.01); *H01L 27/14663* (2013.01); *H01L 31/02322* (2013.01); *H01L 31/02327* (2013.01); *H04N 5/32* (2013.01); *H04N 5/361* (2013.01); *G01T 1/20* (2013.01)

(58) Field of Classification Search
  CPC ......... H01L 27/14609; H01L 27/14603; H01L 27/14623; H04N 5/32; H04N 5/374; H04N 5/357; G01T 1/20
  See application file for complete search history.

(56) References Cited

U.S. PATENT DOCUMENTS

| | | |
|---|---|---|
| 7,381,965 B2 | 6/2008 | Ishii et al. |
| 7,386,089 B2 | 6/2008 | Endo et al. |
| 7,408,167 B2 | 8/2008 | Kameshima et al. |
| 7,514,663 B2 | 4/2009 | Yagi et al. |
| 7,541,591 B2 | 6/2009 | Endo et al. |
| 7,541,617 B2 | 6/2009 | Mochizuki et al. |
| 7,573,038 B2 | 8/2009 | Yokoyama et al. |
| 7,613,277 B2 | 11/2009 | Takenaka et al. |
| 7,629,564 B2 | 12/2009 | Mochizuki et al. |
| 7,645,976 B2 | 1/2010 | Watanabe et al. |
| 7,718,973 B2 | 5/2010 | Endo et al. |
| 7,724,874 B2 | 5/2010 | Kameshima et al. |
| 7,732,776 B2 | 6/2010 | Takenaka et al. |
| 7,750,309 B2 | 7/2010 | Endo et al. |
| 7,750,422 B2 | 7/2010 | Watanabe et al. |
| 7,791,035 B2 | 9/2010 | Yokoyama et al. |
| 7,812,313 B2 | 10/2010 | Mochizuki et al. |
| 7,812,317 B2 | 10/2010 | Watanabe et al. |
| 7,847,263 B2 | 12/2010 | Yagi et al. |
| 7,850,367 B2 | 12/2010 | Takenaka et al. |
| 7,858,947 B2 | 12/2010 | Mochizuki et al. |
| 7,869,568 B2 | 1/2011 | Yokoyama et al. |
| 7,880,145 B2 | 2/2011 | Yagi et al. |
| 7,923,695 B2 | 4/2011 | Ishii et al. |
| 7,932,946 B2 | 4/2011 | Ishii et al. |
| 7,965,817 B2 | 6/2011 | Kameshima et al. |
| 8,067,743 B2 | 11/2011 | Ishii et al. |
| 8,084,745 B2 | 12/2011 | Mochizuki et al. |
| 8,093,562 B2 | 1/2012 | Yokoyama et al. |
| 8,107,588 B2 | 1/2012 | Kameshima et al. |
| 8,154,641 B2 | 4/2012 | Nomura et al. |
| 8,222,611 B2 | 7/2012 | Yagi et al. |
| 8,247,779 B2 | 8/2012 | Kameshima et al. |
| 8,368,027 B2 | 2/2013 | Ishii et al. |
| 8,431,905 B2 | 4/2013 | Kondou ................... 250/370.08 |
| 8,519,344 B2 | 8/2013 | Ishii et al. |
| 8,629,406 B2 | 1/2014 | Okada |
| 8,680,472 B2 | 3/2014 | Mochizuki et al. |
| 8,723,996 B2 | 5/2014 | Yokoyama et al. |
| 8,792,024 B2 | 7/2014 | Takenaka et al. |
| 8,809,795 B2 | 8/2014 | Takenaka et al. |
| 8,829,438 B2 | 9/2014 | Sato et al. |
| 8,878,972 B2 | 11/2014 | Wayama et al. |
| 9,270,903 B2 | 2/2016 | Wayama et al. |
| 9,277,896 B2 | 3/2016 | Ofuji et al. |
| 9,423,513 B2 | 8/2016 | Watanabe et al. |
| 9,521,347 B2 | 12/2016 | Kawanabe et al. |
| 9,625,585 B1 | 4/2017 | Yokoyama et al. |
| 9,661,240 B2 | 5/2017 | Fujiyoshi et al. |
| 9,675,307 B2 | 6/2017 | Ofuji et al. |
| 9,726,767 B2 | 8/2017 | Kawanabe et al. |
| 2010/0148080 A1 | 6/2010 | Endo et al. |
| 2011/0317054 A1 | 12/2011 | Kameshima et al. |
| 2012/0001079 A1 | 1/2012 | Okada ........................ 250/366 |
| 2012/0049077 A1 | 3/2012 | Okada ..................... 250/370.08 |
| 2013/0188079 A1 | 7/2013 | Yorito |
| 2013/0202086 A1* | 8/2013 | Tsuji ..................... H01L 27/144 378/62 |
| 2013/0342514 A1 | 12/2013 | Yokoyama et al. |
| 2014/0151769 A1 | 6/2014 | Wayama et al. |
| 2014/0154833 A1 | 6/2014 | Wayama et al. |
| 2015/0316661 A1* | 11/2015 | Fujiyoshi .............. G01T 1/2018 378/62 |
| 2016/0025865 A1 | 1/2016 | Wayama et al. |
| 2016/0047920 A1* | 2/2016 | Yokoyama ............. G01N 23/04 378/62 |
| 2017/0153336 A1* | 6/2017 | Kawanabe ............... A61B 6/52 |
| 2017/0201704 A1 | 7/2017 | Furumoto et al. |

FOREIGN PATENT DOCUMENTS

| | | |
|---|---|---|
| JP | 2012-015913 | 1/2012 |
| JP | 2012-052896 | 3/2012 |
| JP | 2012-119956 | 6/2012 |
| JP | 2013-195415 | 9/2013 |
| WO | 2011018816 | 2/2011 |

\* cited by examiner

[Fig. 1]
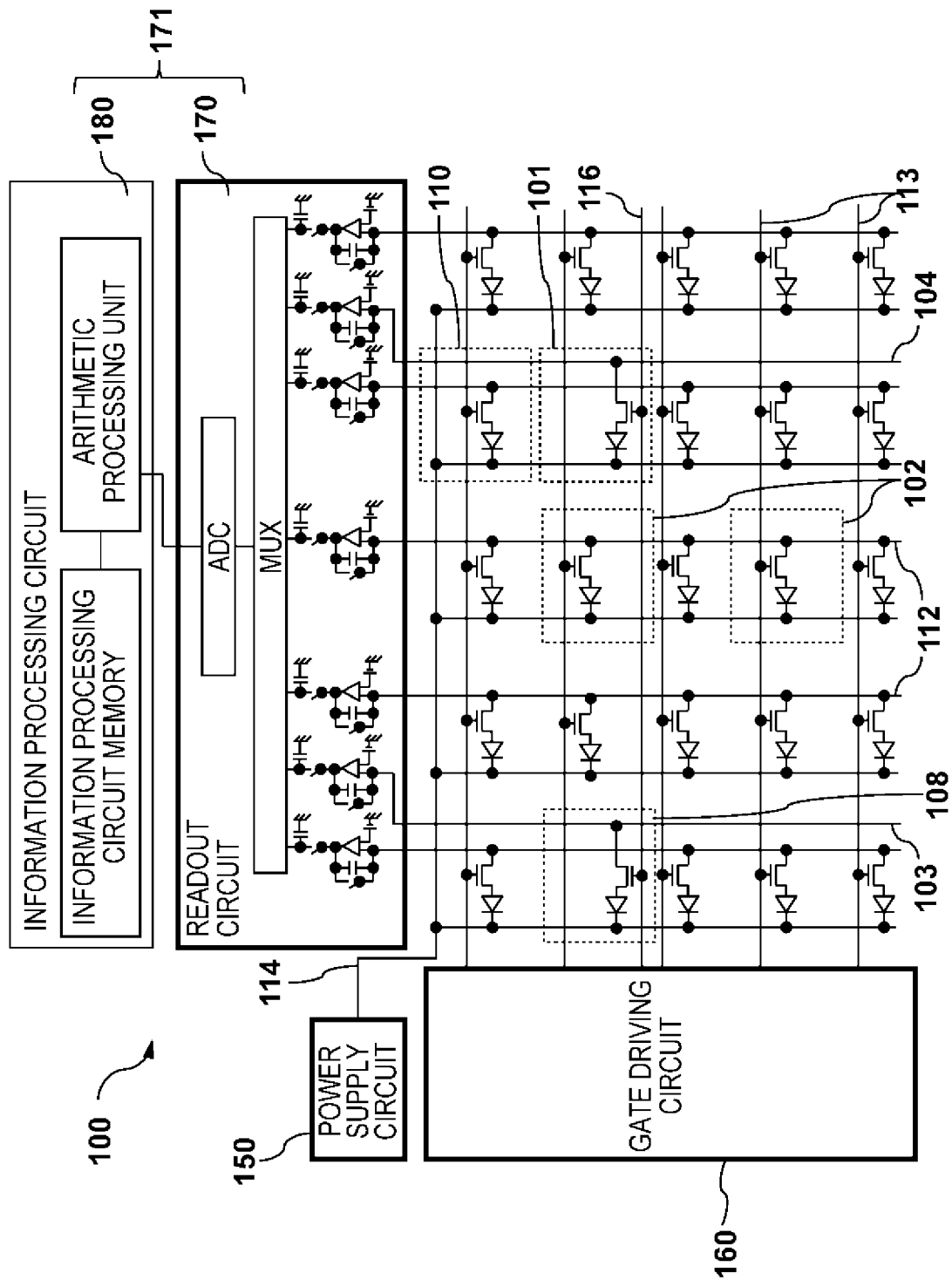

[Fig. 2]
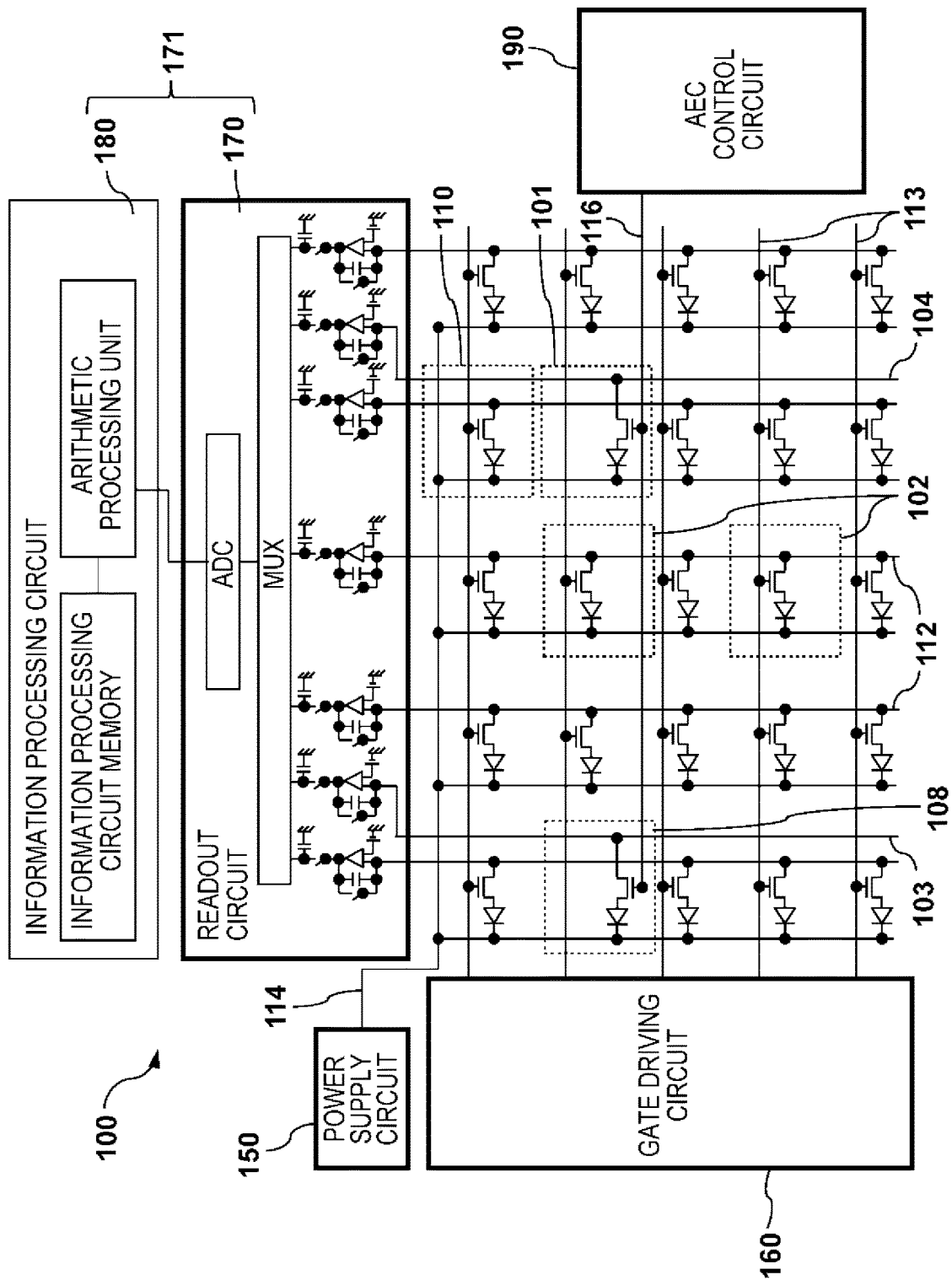

[Fig. 3A]
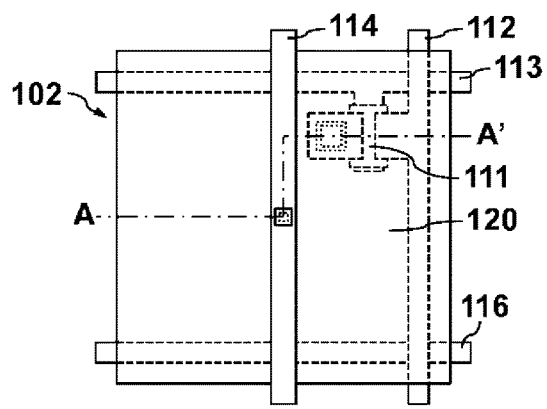
[Fig. 3B]
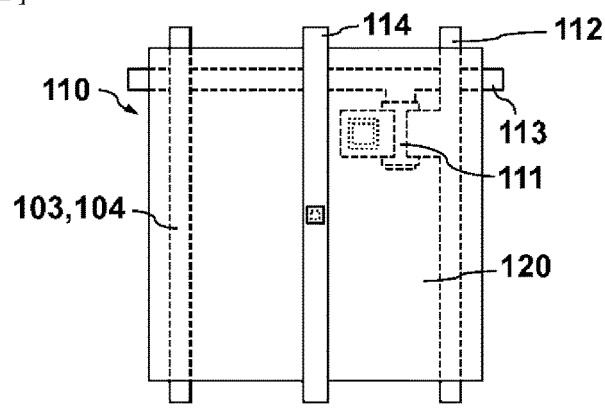
[Fig. 3C]
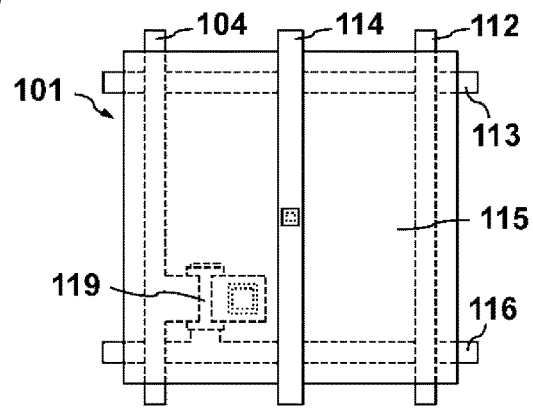
[Fig. 3D]
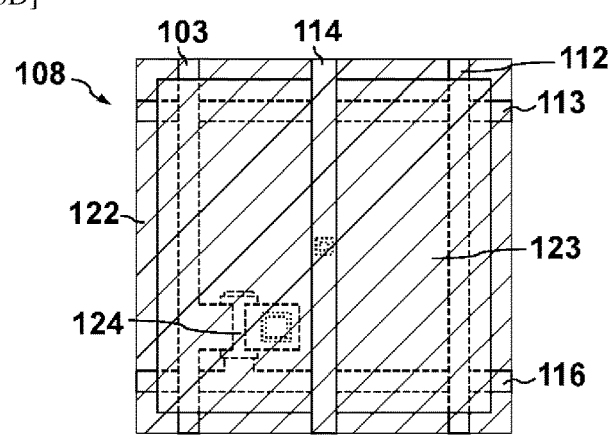

[Fig. 4]
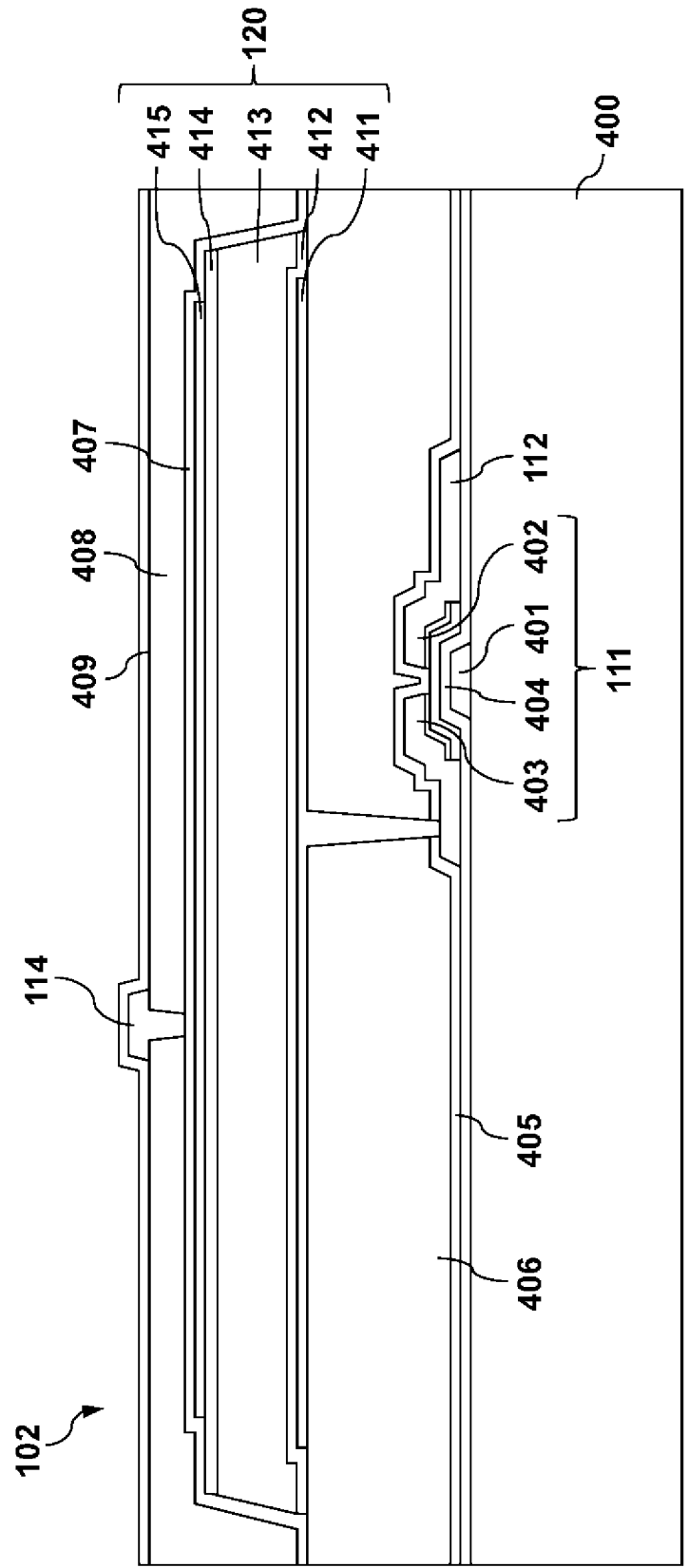

[Fig. 5]
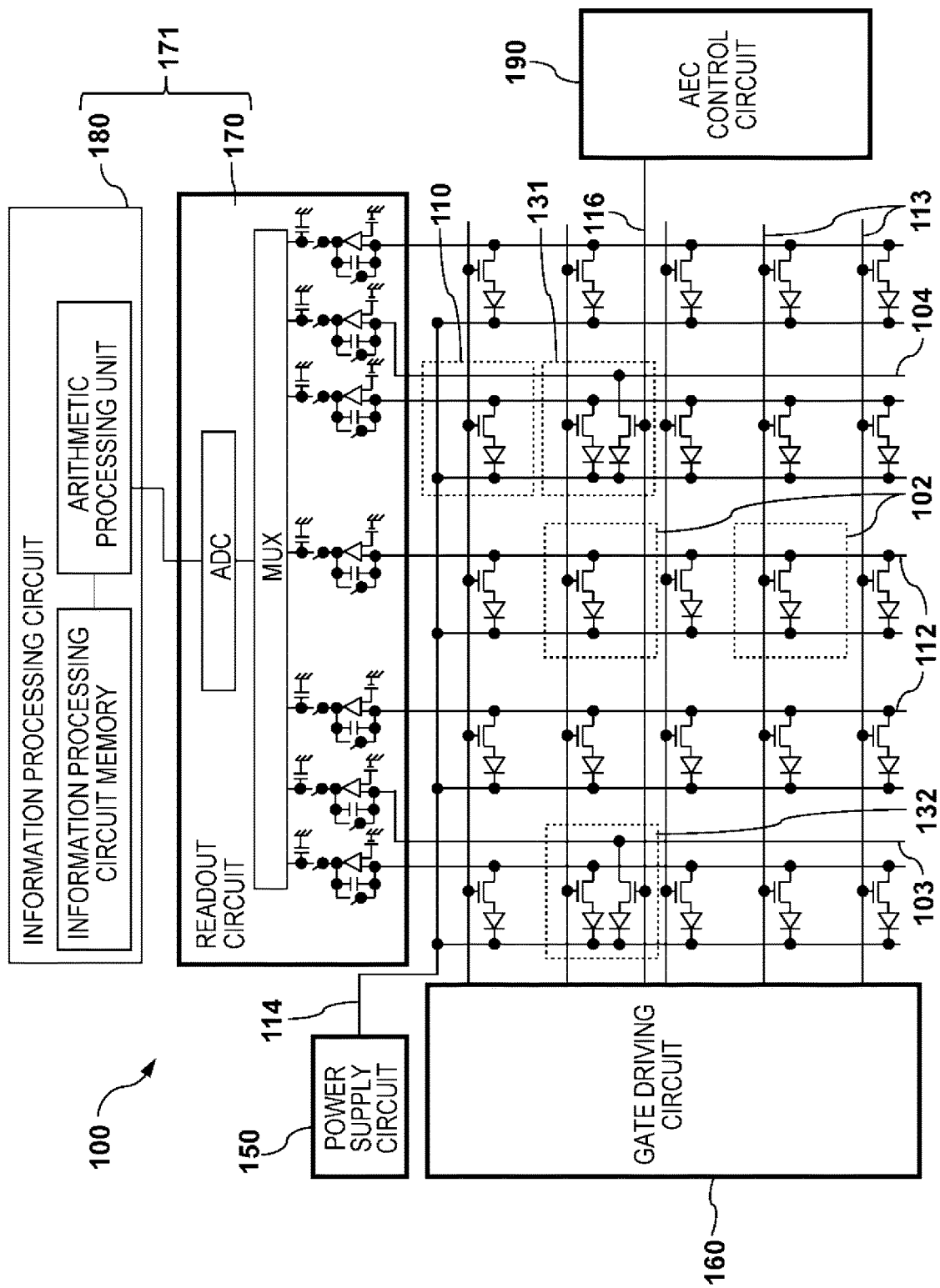

[Fig. 6A]
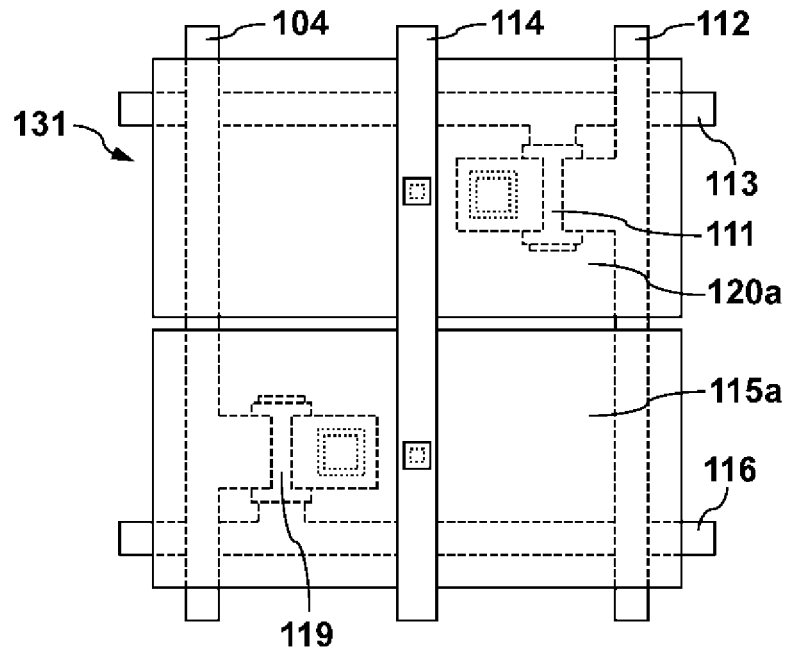
[Fig. 6B]
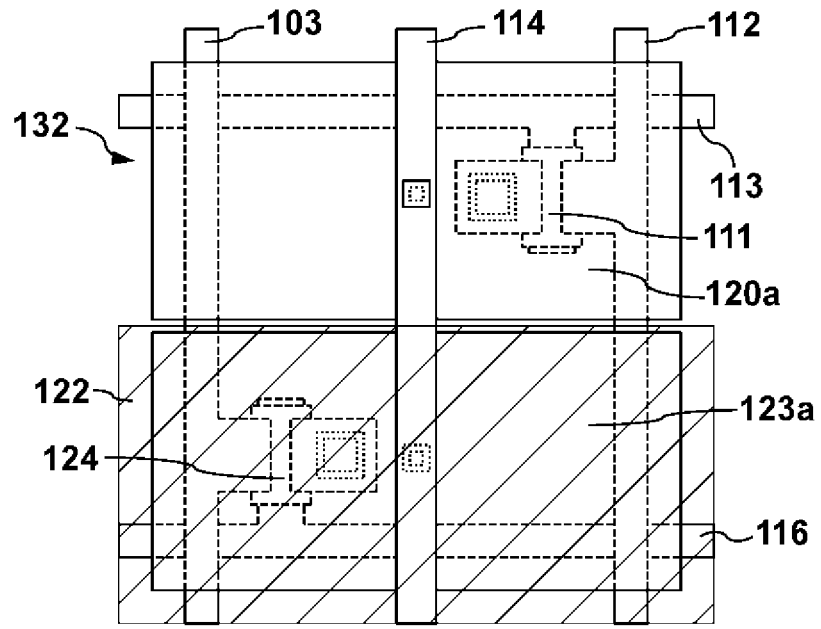

[Fig. 7]
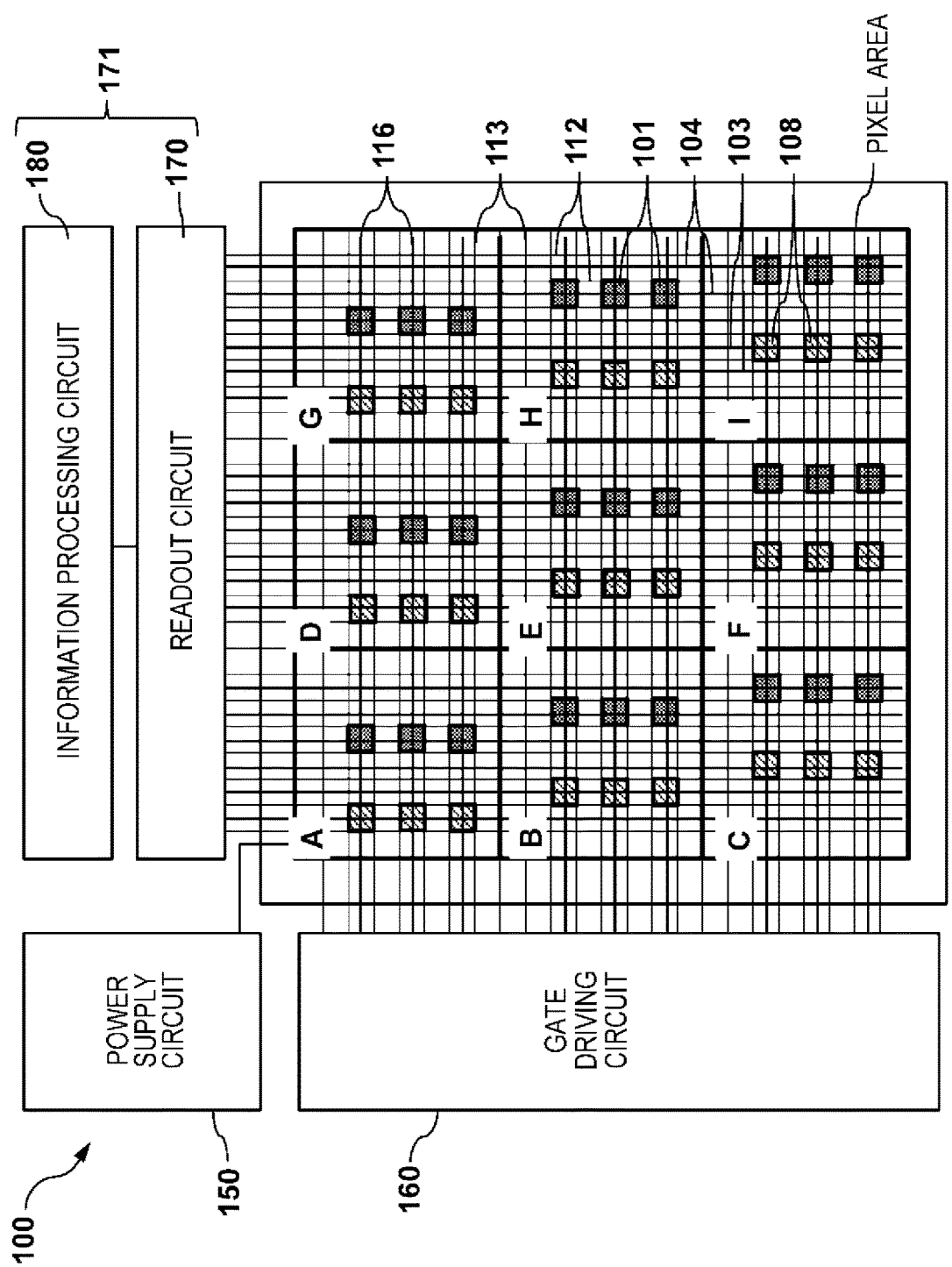

[Fig. 8]
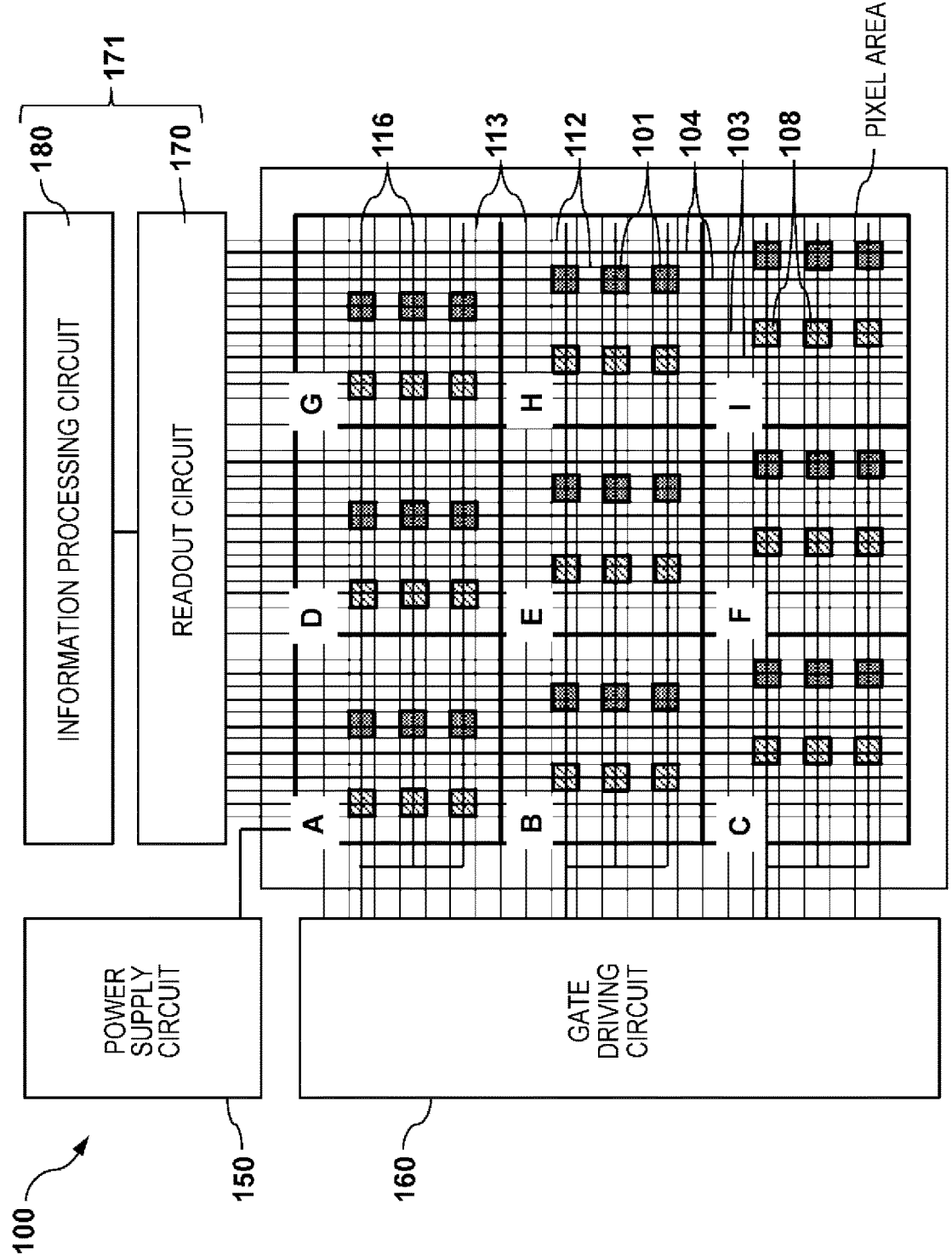

[Fig. 9]
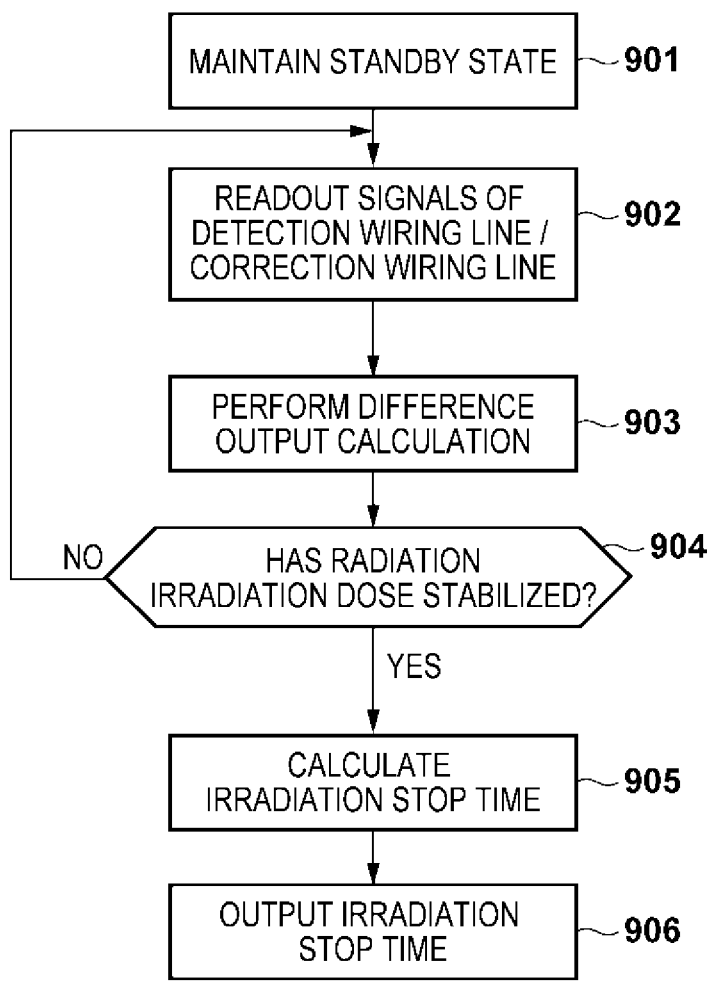

[Fig. 10]
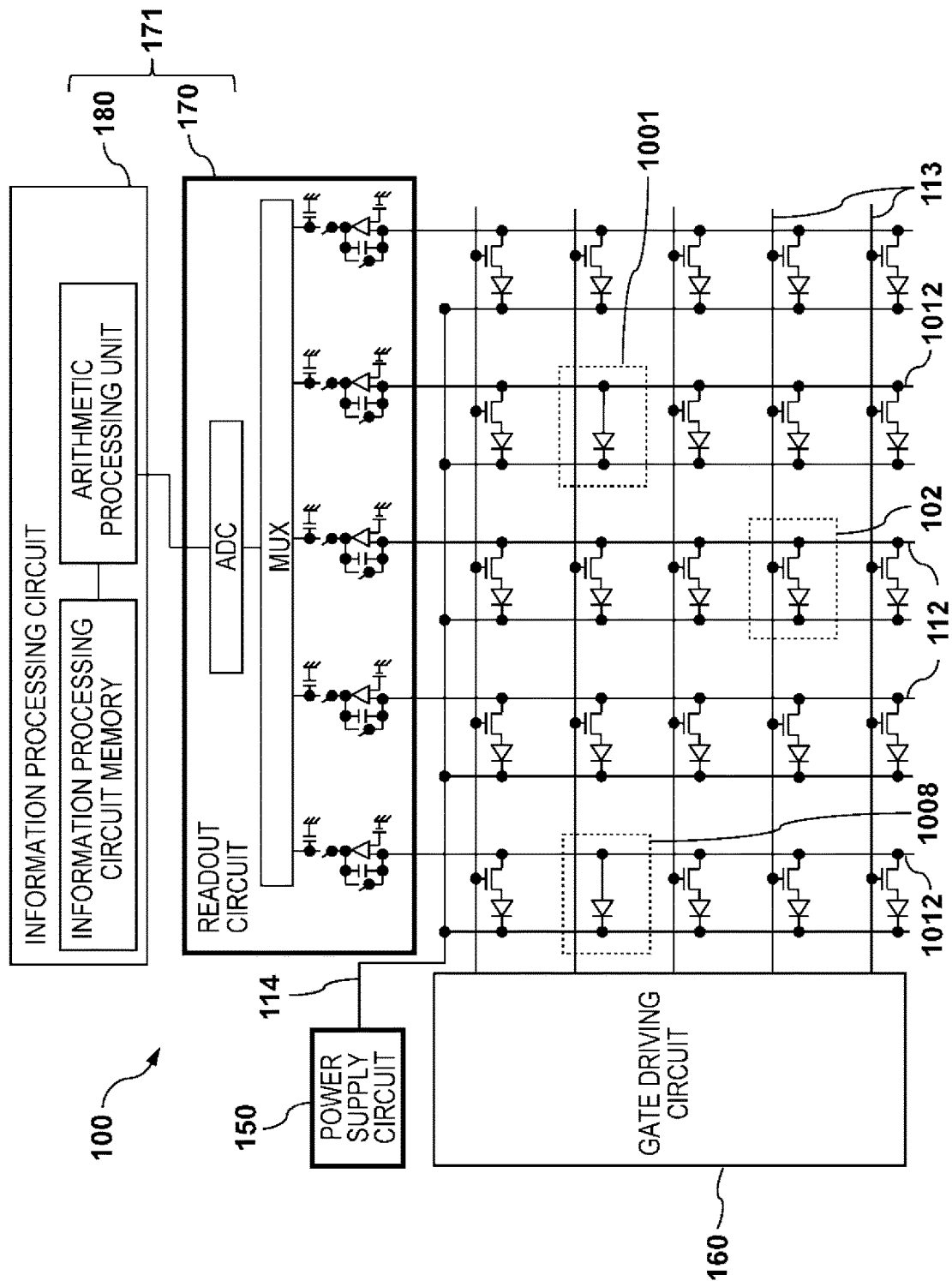

[Fig. 11]
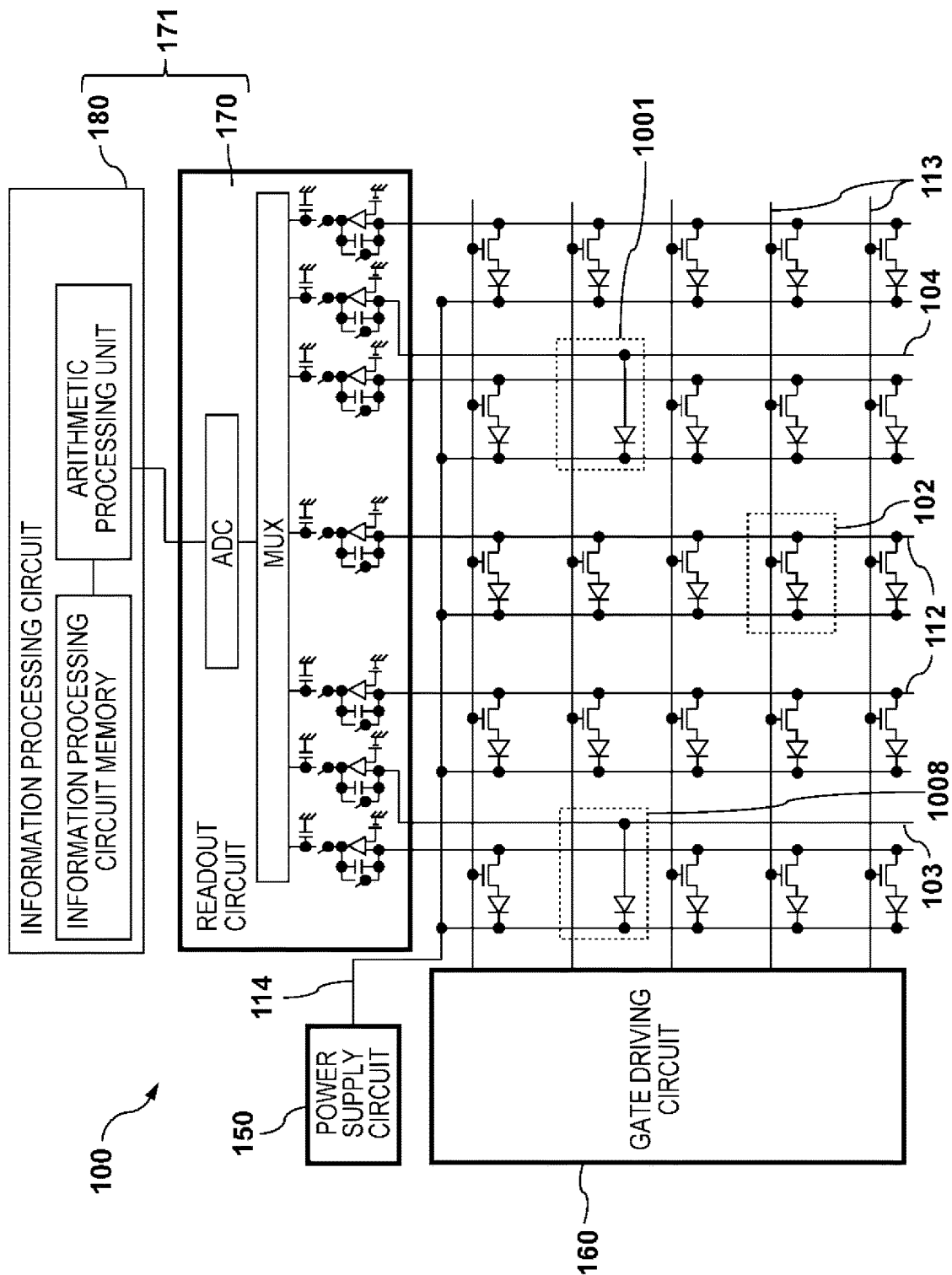

[Fig. 12A]
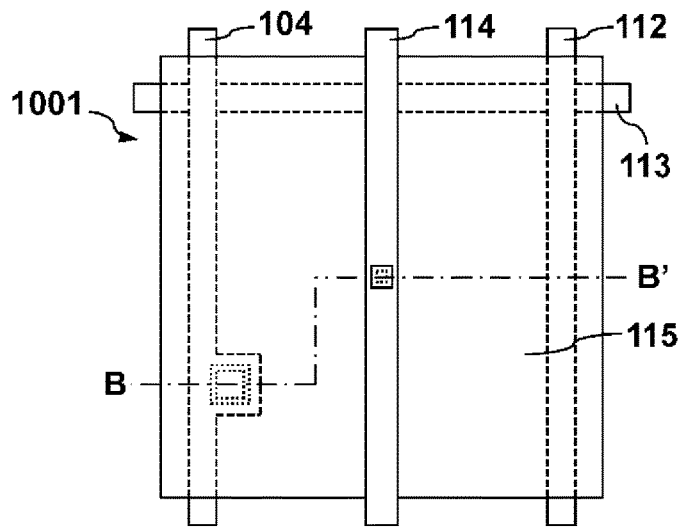
[Fig. 12B]
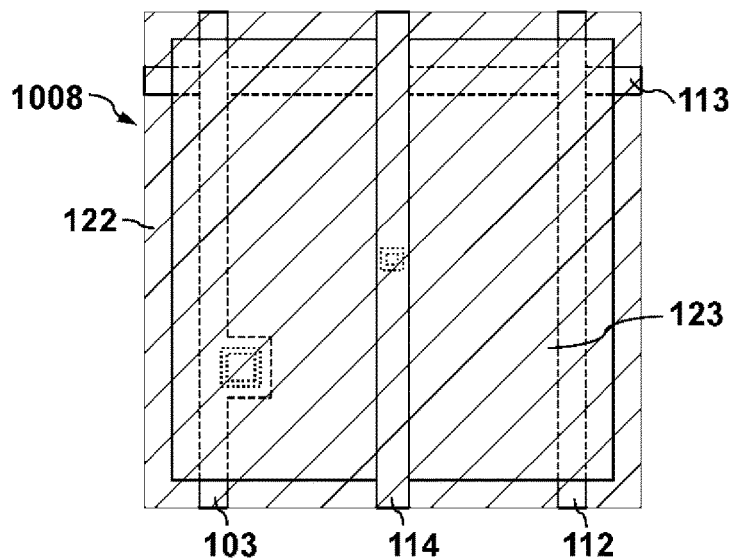
[Fig. 12C]
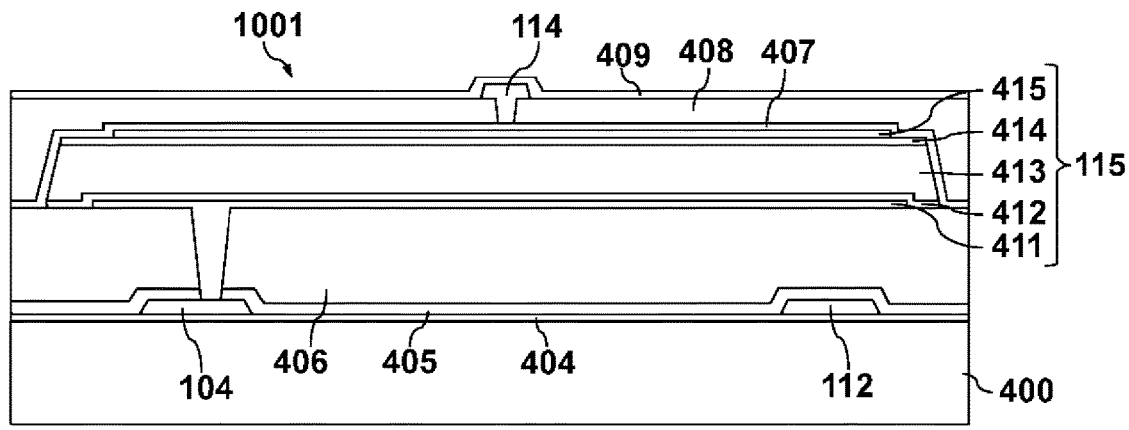

[Fig. 13]
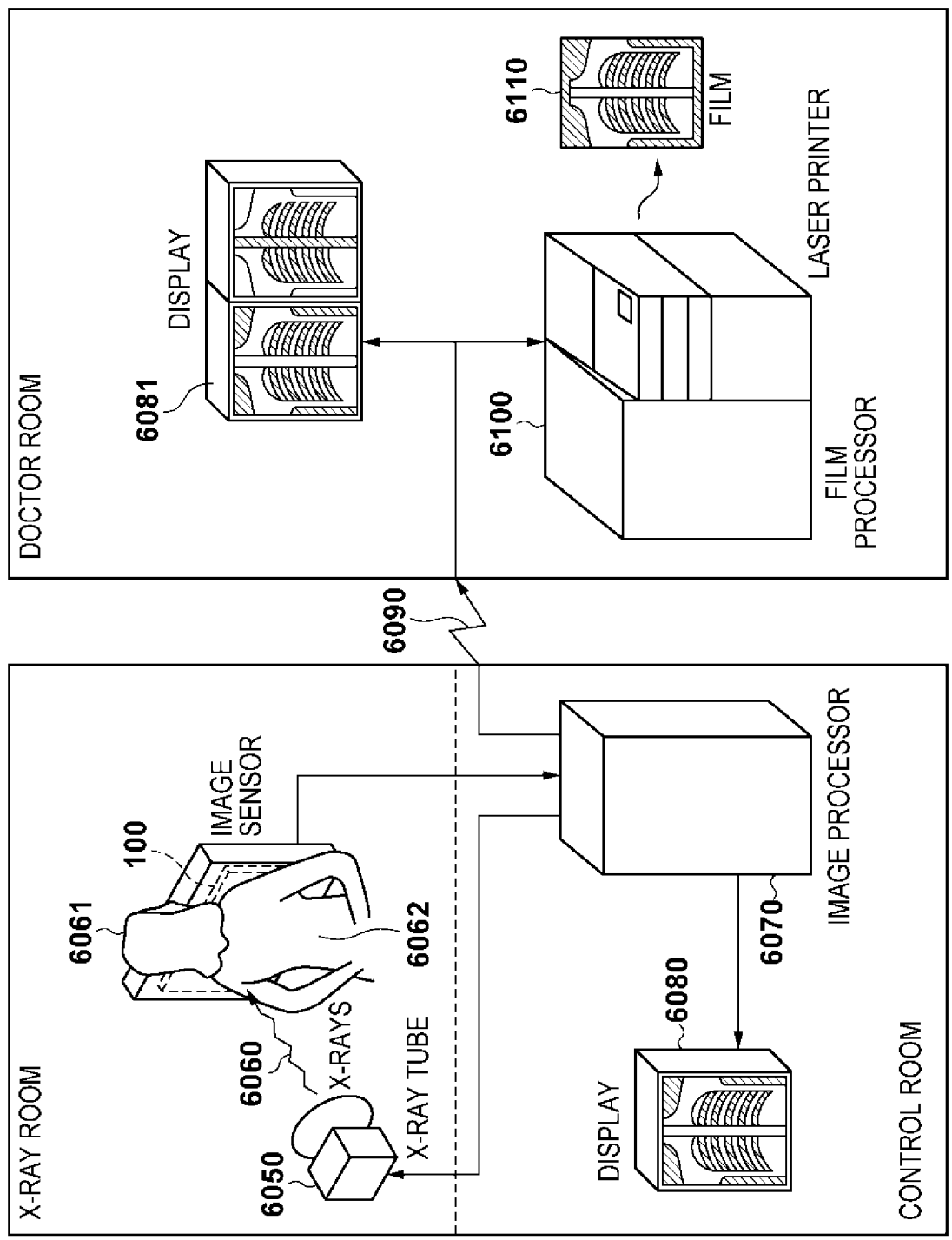

RADIATION IMAGING APPARATUS AND RADIATION IMAGING SYSTEM

TECHNICAL FIELD

The present invention relates to a radiation imaging apparatus and a radiation imaging system.

BACKGROUND ART

A radiation imaging apparatus in which pixels, each combining a conversion element that converts radiation into charges and a switch element such as a thin film transistor (TFT) or the like, are arranged in a two-dimensional array has been widely used. In recent years, in consideration of increasing the multi-functionality of such a radiation imaging apparatus, incorporation of an automatic exposure control (AEC) function is being considered as one such function to be increased. The AEC function is used by a radiation imaging apparatus to obtain radiation irradiation information while radiation is being emitted from the radiation source.

Japanese Patent Laid-Open No. 2012-15913 discloses a radiation imaging apparatus in which a plurality of pixels including imaging pixels and radiation detecting pixels are provided in a matrix in a detection region for detecting radiation. The radiation detecting pixels are used to detect the start and end of radiation irradiation and to detect the cumulative radiation irradiation dose. Japanese Patent Laid-Open No. 2012-52896 discloses a radiation imaging apparatus in which imaging pixels and radiation detecting pixels are arranged and an image wiring line and a radiation detection wiring line to which signals generated in the pixels are output and a signal detection circuit for detecting signals from the image wiring line and the radiation detection wiring line are included. The image wiring line and the radiation detection wiring line have almost the same pattern, but radiation detecting pixels fewer than those on the radiation detection wiring line or no radiation detecting pixels are connected on the image wiring line. The signal detection circuit detects radiation based on a difference between the signal obtained from the image wiring line and the signal obtained from the radiation detection wiring line.

SUMMARY OF INVENTION

In the structure of the radiation imaging apparatus according to Japanese Patent Laid-Open No. 2012-15913, a parasitic capacitor that cannot be ignored is present between an electrode of each imaging pixel and the radiation detection wiring line to which the radiation detecting pixels are connected. Through this parasitic capacitor, crosstalk which transmits potential variation of the electrode of each imaging pixel generated by radiation irradiation to the radiation detection wiring line is generated. In each signal that flows through the radiation detection wiring line, a component of the signal from each radiation detecting pixel and a component generated by crosstalk are included. Due to this crosstalk component, the signal from each radiation detecting pixel during radiation irradiation becomes difficult to obtain.

In the method disclosed in Japanese Patent Laid-Open No. 2012-52896, a component of the signal from each radiation detecting pixel is obtained by obtaining the difference between signals obtained from the image wiring line and the radiation detection wiring line. The component generated by crosstalk can be reduced by obtaining the difference of signals obtained from the image wiring line and the radiation detection wiring line having almost the same wiring pattern. Meanwhile, due to temperature changes at the time of driving the radiation imaging apparatus, characteristics such as the offset level of the switch element and the dark current of the conversion element used in each pixel are changed. When radiation is to be detected, radiation detecting pixels are turned on to operate and the switch element of each imaging pixel is turned off. The difference of signals obtained from the image wiring line and the radiation detection wiring line in this case has not only components due to incident radiation but is also superimposed with change components of characteristics such as the offset level and the dark current of the radiation detecting pixel turned on and operating. Due to the change in the characteristics such as the offset level and the dark current of each radiation detecting pixel, the signal from each radiation detecting pixel can change, and accurate detection of radiation may be impossible.

Some embodiments of the present invention provide a technique for improving the precision of radiation detection by correcting the change in pixel characteristics due to crosstalk between a pixel and a wiring line or temperature change at the time of driving.

According to some embodiments, a radiation imaging apparatus comprising a plurality of pixels arranged in an array in an image sensing region and configured to obtain a radiation image, at least one first detecting element and at least one second detecting element each including a conversion element configured to convert radiation into an electrical signal to obtain radiation irradiation information including at least one of start of radiation irradiation, end of radiation irradiation, a radiation irradiation intensity, and a radiation irradiation dose, a first signal line to which a signal from the first detecting element is to be output and a second signal line to which a signal from the second detecting element is to be output, and a signal processing circuit configured to process the signal output from the first detecting element via the first signal line and the signal output from the second detecting element via the second signal line, wherein the first signal line and the second signal line are arranged in the image sensing region or arranged adjacent to the image sensing region, the first detecting element has a larger region to detect radiation than the second detecting element, and the signal processing circuit generates the radiation irradiation information based on the signal from the first signal line and the signal from the second signal line, is provided.

According to some other embodiments, a radiation imaging system comprising a radiation imaging apparatus and a signal processing unit, wherein the radiation imaging apparatus comprises a plurality of pixels arranged in an array in an image sensing region and configured to obtain a radiation image, at least one first detecting element and at least one second detecting element each including a conversion element configured to convert radiation into an electrical signal to obtain radiation irradiation information including at least one of start of radiation irradiation, end of radiation irradiation, a radiation irradiation intensity, and a radiation irradiation dose, a first signal line to which a signal from the first detecting element is to be output and a second signal line to which a signal from the second detecting element is to be output, and a signal processing circuit configured to process the signal output from the first detecting element via the first signal line and the signal output from the second detecting element via the second signal line, wherein the first signal line and the second signal line are arranged in the image sensing region or arranged adjacent to the image sensing region, the first detecting element has a larger region to detect radiation than the second detecting element, the signal processing circuit generates the radiation irradiation information based on the signal from the first signal line and the signal from the second signal line, and the signal processing unit is configured to process a signal from the radiation imaging apparatus, is provided.

Further features of the present invention will become apparent from the following description of exemplary embodiments (with reference to the attached drawings).

BRIEF DESCRIPTION OF THE DRAWINGS

FIG. 1 is an equivalent circuit diagram showing the circuit arrangement of a radiation imaging apparatus according to an embodiment of the present invention;

FIG. 2 is an equivalent circuit diagram showing a modification of the circuit arrangement of the radiation imaging apparatus of FIG. 1;

FIG. 3A is a plan view of a pixel, a detecting element, and a correction element of the radiation imaging apparatus of FIG. 1;

FIG. 3B is a plan view of a pixel, a detecting element, and a correction element of the radiation imaging apparatus of FIG. 1;

FIG. 3C is a plan view of a pixel, a detecting element, and a correction element of the radiation imaging apparatus of FIG. 1;

FIG. 3D is a plan view of a pixel, a detecting element, and a correction element of the radiation imaging apparatus of FIG. 1;

FIG. 4 is a sectional view of the pixel of the radiation imaging apparatus of FIG. 1;

FIG. 5 is an equivalent circuit diagram showing another modification of the circuit arrangement of the radiation imaging apparatus of FIG. 1;

FIG. 6A is a plan view of pixels of the radiation imaging apparatus of FIG. 5;

FIG. 6B is a plan view of pixels of the radiation imaging apparatus of FIG. 5;

FIG. 7 is a view showing the schematic layout of the radiation imaging apparatus of FIG. 1;

FIG. 8 is a view showing a modification of the view showing the schematic layout of the radiation imaging apparatus of FIG. 7;

FIG. 9 is a flowchart showing an operation of the radiation imaging apparatus of FIG. 1;

FIG. 10 is an equivalent circuit diagram showing the circuit arrangement of a radiation imaging apparatus according to an embodiment of the present invention;

FIG. 11 is an equivalent circuit diagram showing a modification of the circuit arrangement of the radiation imaging apparatus of FIG. 10;

FIG. 12A is a plan view of a detecting element;

FIG. 12B is a plan view of a correction element according to the radiation imaging apparatus of FIG. 10;

FIG. 12C is a sectional view of a detecting element;

FIG. 13 is a view for explaining an example of the arrangement of a radiation imaging system using a radiation imaging apparatus according to an embodiment of the present invention.

DESCRIPTION OF EMBODIMENTS

A detailed embodiment of a radiation imaging apparatus according to the present invention will now be described with reference to the accompanying drawings. Note that in the following description and drawings, common reference numerals denote common components throughout a plurality of drawings. Hence, the common components will be described by cross-referring to the plurality of drawings, and a description of components denoted by common reference numerals will appropriately be omitted. Note that radiation according to the present invention can include not only α-rays, β-rays, and γ-rays that are beams generated by particles (including photons) emitted by radioactive decay but also beams having energy equal to or higher than the energy of these beams, for example, X-rays, particle beams, and cosmic rays.

A radiation imaging apparatus according to a first embodiment will be described with reference to FIGS. 1 to 9. FIG. 1 is an equivalent circuit diagram showing the circuit arrangement of a radiation imaging apparatus 100 according to this embodiment. The radiation imaging apparatus 100 according to this embodiment includes an image sensing region in which a plurality of pixels are arranged in an array on a substrate and a peripheral region for controlling each pixel or processing an electrical signal output from each pixel.

The peripheral region includes a power supply circuit 150 and a gate driving circuit 160 for driving and controlling each pixel and a signal processing circuit 171 which includes a readout circuit 170 and an information processing circuit 180 for processing the electrical signal output from each pixel. However, the present invention is not limited to this. For example, the readout circuit 170 and the information processing circuit 180 can be formed integrally.

The image sensing region includes a plurality of pixels for obtaining a radiation image and a plurality of detecting elements for detecting radiation irradiation and obtaining radiation irradiation information. In this embodiment, there are included, depending on the arrangement of the wiring lines in each pixel, pixels 102, and pixels 110 each having a signal line for transferring an electrical signal obtained by the detecting element to the signal processing circuit 171 running through the pixel. Also, as detecting elements, there are a detecting element 101 as the first detecting element and a correction element 108 as the second element that respectively output electrical signals to the signal processing circuit by different signal lines. The detecting element 101 and the correction element 108 are used to obtain, in the case of radiation irradiation, radiation irradiation information that is different from the radiation image and is information related to the start of radiation irradiation, the end of radiation irradiation, the radiation irradiation intensity, the radiation irradiation dose, or the like. By arranging such detecting element 101 and correction element 108, it becomes possible to incorporate an automatic exposure control (AEC) function in the radiation imaging apparatus 100. Although FIG. 1 shows that 5×5 (rows×columns) pixels are provided in the image sensing area, this is an equivalent circuit diagram representing only a part of the image sensing region of the radiation imaging apparatus 100.

The image sensing region can have only one or a plurality of pixel areas in which these detecting element 101 and correction element 108 are arranged. In the radiation imaging apparatus 100, pixel areas each arranged with the detecting element 101 and correction element 108 are arranged in, for example, a 3×3 or 5×5 matrix. This allows radiation irradiation information of each irradiated pixel area of the radiation imaging apparatus 100 to be separately detected for each pixel area. A description of an image sensing region that includes a plurality of pixel areas will be given later with reference to FIGS. 7 and 8.

The pixels 102 and 110 arranged in the image sensing region of the radiation imaging apparatus 100 are supplied with a power supply voltage from the power supply circuit 150 via a power supply wiring line 114 and controlled by the gate driving circuit 160 via a corresponding image control wiring line 113. The electrical signals output from the pixels 102 and 110 are transferred to the signal processing circuit 171 by a corresponding image signal line 112. This allows a radiation image to be obtained. The detecting element 101 and the correction element 108 are also supplied with a power supply voltage from the power supply circuit 150 via the power supply wiring line 114 and controlled by the gate driving circuit 160 via a detection control wiring line 116. An electrical signal output from the detecting element 101 is transferred to the signal processing circuit 171 by a detection signal line 104 serving as a first signal line. An electrical signal output from the correction element 108 is transferred to signal processing circuit 171 by a correction signal line 103 serving as a second signal line. By using the detecting element 101 and the correction element 108 to obtain radiation irradiation information, it becomes possible to obtain radiation irradiation information such as the radiation irradiation dose of the region in which the detecting element 101 and the correction element 108 are arranged. In this embodiment, the detection signal line 104 and the correction signal line 103 are arranged in the image sensing region. Alternatively, the detection signal line 104 and the correction signal line 103 can also be arranged adjacent to each other at the edge of the image sensing region.

In the radiation imaging apparatus 100, parts other than the detecting element 101 or the correction element 108 are irradiated with radiation. Upon radiation irradiation, charges corresponding to the radiation irradiation dose are generated and accumulated in the pixels 102 and 110. In this case, in each pixel 110 that the detection signal line 104 runs through, the accumulated charges are transferred to the detection signal line 104 based on charge conservation via a parasitic capacitor that is present between the detection signal line 104 and the electrode of a conversion element of the pixel 110 which converts the radiation into charges. As a result, the amount of charges serving as the electrical signal read out from the detection signal line 104 will inevitably include two components, that is, the charges from the detecting element 101 and the charges transferred from each pixel 110 via the capacitor between the detection signal line 104 and the conversion element of the pixel 110. Hence, for example, if the radiation irradiation area expands and the number of pixels 110 to be irradiated with radiation increases, the amount of charges to be transferred from each pixel 110 to the detection signal line 104 will increase. Also, for example, if the radiation irradiation area becomes smaller and the number of pixels 110 that have accumulated a large amount of charges by radiation irradiation decreases, the amount of charges to be transferred from each pixel 110 to the detection signal line 104 is reduced.

The correction signal line 103 is used to correctly read out an electrical signal corresponding to the radiation irradiation dose that the detecting element 101 is irradiated with by correcting the transfer of charges via the capacitor between the detection signal line 104 and pixels 110 that the detection signal line 104 runs through. For example, if the correction signal line 103 and the detection signal line 104 have the same shape and/or run through the same number of pixels 110, the parasitic capacitor existing between each pixel 110 and the correction signal line 103 and that existing between each pixel 110 and the detection signal line 104 become almost equal. As a result, the amount of charges respectively transferred from each pixel 110 to the correction signal line 103 and that transferred from each pixel 110 to the detection signal line 104 become almost equal. By subtracting the amount of charges as the value of the electrical signal from the correction signal line 103 from the amount of charges as the value of the electrical signal obtained by the detection signal line 104, an amount of charges equal to the amount of charges converted in the detecting element 101 can be generated and obtained as signal information of the detecting element 101. Various methods can be used as the subtraction method in this case. For example, analog subtraction or digital subtraction can be used. Alternatively, a correlated double sampling (CDS) circuit may be used.

However, the signal processing circuit 171 and the like arranged in the periphery of the image sensing region generates heat at the time of signal processing. Due to this local heat generation, the image sensing region in which the pixels 102 and 110 and the detecting element 101 are arranged may change because of uneven temperature or temperature distribution. In some cases, if the temperature changes in a conversion element and a thin film transistor (TFT) serving as a switch element that are arranged in each of the pixels 102 and 110 and the detecting element 101, characteristics such as the dark current of the conversion element and the offset level of the TFT may change. When detecting radiation, the detecting element 101 is turned on to operate and the TFTs of the respective pixels 102 and 110 are turned off. In this case, the electrical signal difference between the correction signal line 103 and the detection signal line 104 is not only superimposed with a component due to incident radiation but also superimposed with change components of characteristics such as the offset level or the dark current of the detecting element 101 turned on to operate. If characteristics such as the dark current and the offset level of the detecting element 101 change, the value of the electrical signal obtained by the difference also changes. For example, if the offset level of the detecting element 101 increases because of a rise in temperature, the extracted electrical signal may exceed the threshold for detecting radiation even if there is no radiation irradiation. In such a case, it may be recognized that radiation irradiation has been performed even if no radiation irradiation has been performed.

In contrast, in this embodiment, the correction element 108, which is connected to the correction signal line 103 and has the same conversion element structure and the same TFT structure as the detecting element 101 connected to the detection signal line 104, is arranged in the image sensing region of the radiation imaging apparatus 100. The correction element 108 can be turned on to operate simultaneously with the detecting element 101. In FIG. 1, the correction element 108 and the detecting element 101 are controlled via the same detection control wiring line 116 and turned on to operate simultaneously. The correction element 108 may be arranged near the detecting element 101. If the surrounding temperature and temperature distribution of the detecting element 101 of the image sensing region change, characteristics such as the dark current and the offset level of each of the pixels 102 and 110 and the detecting element 101 are changed. However, by arranging the correction element 108 which has the same temperature characteristic and is arranged nearby, even if characteristics such as the dark current and the offset level of the detecting element 101 change, the dark current and the offset level can be subtracted. As a result, it becomes possible to accurately generate and obtain information related to radiation irradiating the detecting element 101.

However, since the correction element 108 and the detecting element 101 have the same conversion element and TFT structure, as described above, the difference between the amounts of charges serving as the electrical signals respectively output for the incident radiation amounts from the correction element 108 and the detecting element 101 is small. If the difference between the respective outputs of the correction element 108 and the detecting element 101 is small, it is difficult to obtain the signal information of the detecting element 101 just by obtaining the difference between the respective amounts of charges of the detection signal line 104 and the correction signal line 103. To generate radiation irradiation information, the detecting element 101 and the correction element 108 need to respectively output different electrical signals for the incident radiation while having the same conversion element and TFT structures. To output different electrical signals, the sensitivity for converting incident radiation into an electrical signal can be different in the detecting element 101 and the correction element 108. In this embodiment, the size of the radiation detection region is different in the detecting element 101 and the correction element 108, and the radiation detection region of the detecting element 101 is formed to be larger than that of the correction element 108. For example, in the case of a radiation imaging apparatus that directly converts radiation into electrical signals, a shielding member using a heavy metal such as lead can be provided, as the shielding member to shield radiation, on the conversion element of the correction element 108. In the case of an indirect-type radiation imaging apparatus that converts radiation into light by using a scintillator and converts the light into an electrical signal, for example, an aluminum shielding film or the like can be provided, as the shielding member to shield light, between the conversion element of the correction element 108 and the scintillator. In either conversion type of the radiation imaging apparatus, it may be for the shielding member to be arranged in a region that at least partially overlaps the conversion element of the correction element 108 in planar view with respect to the image sensing region. As a result, the sensitivity of the correction element 108 to convert radiation into an electrical signal becomes lower than that of the detecting element 101. Therefore, the radiation irradiation information can be generated more accurately by subtracting electrical signals respectively obtained from the detection signal line 104 and the correction signal line 103 not only when the parasitic capacitor between each pixel 110 and the detecting element 101 changes but also when the operation temperature changes and the characteristics of the elements change.

For example, in the case of the indirect-type radiation imaging apparatus using the scintillator, the correction element 108 can be the same size and have the same conversion element and TFT structures as the detecting element 101, and a shielding member using, for example, aluminum or chrome for shielding light can be formed on the nearer side that the radiation enters than the conversion element. The shielding member can be arranged, for example, between the scintillator and the conversion element. In addition, for example, the correction element 108 can be entirely covered by a shielding film so that almost no light will be detected and obtain the dark current of the conversion element and the offset level of TFT portion to perform correction of the detecting element 101 by using the obtained values.

The detecting element 101 and the correction element 108 can be arranged adjacent to each other. Alternatively, a number of columns, for example, two columns as shown in FIG. 1, of the pixels 102 can be arranged between the detecting element 101 and the correction element 108. If the detecting element 101 and the correction element 108 are arranged adjacent to each other, the interval between pixels 102 which are sandwiched between the detecting element 101 and the correction element 108 becomes wide. By inserting the pixels 102 between the detecting element 101 and the correction element 108, image correction of the portions of the detecting element 101 and the correction element 108 where pixels are missing becomes easy. The size of each side of the pixels used in the radiation imaging apparatus 100 is small and about, for example, 50 μm to 500 μm. Even in the case in which two pixels 102 are arranged in-between, the relative distance between the detecting element 101 and the correction element 108 is close at about 150 μm to 1.5 mm, and it can be assumed that the temperature environments of the detecting element 101 and the correction element 108 are the same. Even in a case in which a number of columns of the pixels 102 are arranged between the detecting element 101 and the correction element 108, the radiation irradiation information can be accurately generated and obtained.

FIG. 2 is an equivalent circuit diagram showing the circuit arrangement of the radiation imaging apparatus 100 according to this embodiment and shows a modification of the circuit arrangement shown in FIG. 1. A difference with the equivalent circuit diagram shown in FIG. 1 is that the detection control wiring line 116 which controls the detecting element 101 and the correction element 108 is controlled by an AEC control circuit 190 that is separately provided from the gate driving circuit 160 controlling the pixels 102 and 110. The remaining points can be the same as the circuit arrangement as in the equivalent circuit diagram shown in FIG. 1. In this arrangement, the gate driving circuit 160 does not need to perform a complicated operation compared to the gate driving circuit 160 of the radiation imaging apparatus 100 shown in FIG. 1, and it becomes easy to design the driving circuit. For example, during the period in which radiation irradiation is performed and until radiation irradiation information is read out in each of the detecting element 101 and the correction element 108, the AEC control circuit 190 is driven. Subsequently, when the signals for obtaining a radiation image are to be respectively read out from the pixels 102 and 110, the AEC control circuit 190 is stopped and the gate driving circuit 160 can be driven to sequentially read out the signals. The circuit to cause the peripheral region circuits to operate separately for the detecting element 101 and the correction element 108 and for the pixels 102 and 110 is not limited to a control circuit. For example, processing can be performed by providing separate readout circuits for the pixels 102 and 110 and for the signals from the detection signal line 104 and the correction signal line 103 in the readout circuit 170 of the signal processing circuit 171.

FIGS. 3A to 3D show planar views of the pixel 102, the pixel 110, the detecting element 101, and the correction element 108, respectively. FIG. 3A shows a plan view of the pixel 102. In this embodiment, the radiation imaging apparatus 100 is an indirect-type radiation imaging apparatus, and a scintillator (not shown) is arranged above the image sensing region in which pixels 102 and 110, the detecting element 101, and the correction element 108 are arranged. In each pixel 102, a photoelectric conversion element 120 serving as a conversion element for converting the light converted from radiation via the scintillator into an electrical signal is arranged. A thin film transistor (TFT) 111 serving as a switch element and various types of wiring lines are arranged below the photoelectric conversion element 120. An electrical signal generated by photoelectric conversion in the photoelectric conversion element 120 is output to the image signal line 112 via the TFT 111 when the TFT 111 changes to the ON state in accordance with the signal of the image control wiring line 113. The upper electrode of the photoelectric conversion element 120 is connected to the power supply wiring line 114 which applies a constant voltage. The detection control wiring line 116 runs under the photoelectric conversion element 120. Although there are pixels 102 that the detection control wiring line 116 does not run through as shown in FIGS. 1 and 2, FIG. 3A shows a pixel 102 that the detection control wiring line 116 runs through.

FIG. 3B shows the pixel 110 in which the detection signal line 104 or the correction signal line 103 runs through. The rest of the arrangement, other than the point that the detection signal line 104 or the correction signal line 103 runs through the pixel, is the same as the pixel 102. The lower electrode of the photoelectric conversion element 120 arranged in each of the pixels 102 and 110 serves as a separate electrode for each pixel. Therefore, in a planar view with respect to the image sensing region, a capacitor is formed in accordance with an overlapping area on a region where the detection signal line 104 or the correction signal line 103 which runs through the pixel 110 and the lower electrode of the photoelectric conversion element 120 overlap. Through this capacitor, based on charge conservation, charges accumulated in the photoelectric conversion element 120 are transferred to the detection signal line 104 or the correction signal line 103.

FIG. 3C shows the detecting element 101. The lower electrode of a photoelectric conversion element 115 is connected to the detection signal line 104 via a TFT 119, and an electrical signal is output from the photoelectric conversion element 115 to the detection signal line 104 when the TFT 119 changes to the ON state in accordance with the signal from the detection control wiring line 116. The TFT 119 is turned on/off to obtain radiation irradiation information by measuring the illuminance in the case of radiation irradiation, detecting the start/end of radiation irradiation, and the like, and the signals accumulated in the photoelectric conversion element 115 are read out.

FIG. 3D shows the correction element 108. The correction element 108 includes a shielding member 122 between the scintillator (not shown) arranged above the image sensing region and a photoelectric conversion element 123. In this embodiment, the photoelectric conversion element 123 arranged on the correction element 108 is entirely covered by the shielding member 122. By arranging the shielding member 122, a difference occurs between the output value of electrical signals of the incident radiation of the photoelectric conversion element 115 of the detecting element 101 and that of the photoelectric conversion element 123 of the correction element 108. Structures other than this can be the same as the detecting element 101 shown in FIG. 3C. The lower electrode of the photoelectric conversion element 123 is connected to the correction signal line 103 via a TFT 124, and an electrical signal from the photoelectric conversion element 123 is output to the correction signal line 103 when the TFT 124 changes to the ON state in accordance with the signal from the detection control wiring line 116.

As described above, charges generated in the photoelectric conversion element 120 are output to the detection signal line 104 in accordance with the capacitor formed between the detection signal line 104 and the photoelectric conversion element 120 of each pixel 110. There are a number of such pixels 110 in the image sensing region, and the signals written by the capacitive coupling between the photoelectric conversion elements 120 of respective pixels 110 and the detection signal line 104 cannot be ignored. For example, if there are several hundreds to several thousands of these pixels 110, there can be a case in which the signal amount due to capacitive coupling becomes several times to several tens of times of the electrical signal from the detecting element 101. In addition, for example, even in a case in which the photoelectric conversion element 120 does not overlap the detection signal line 104, charges from the photoelectric conversion element 120 are transferred due to the influence of electric field expansion. Therefore, by arranging the correction signal line 103 in a nearby region and obtaining each signal difference, signals to be transferred from such photoelectric conversion elements 120 can be reduced and the signal from the detecting element 101 can be read out.

FIG. 4 shows a sectional view taken along a line A-A' of the pixel 102 shown in FIG. 3A. Pixels and elements are formed on a substrate 400 of the image sensing region. An insulating substrate can be used as the substrate 400 in this embodiment. As the substrate 400, for example, a glass substrate or a plastic substrate can be used. The TFT 111 serving as a switch element is formed on the substrate 400. Although an inversely staggered TFT is used in this embodiment, a top gate TFT may be used. The TFT 111 includes a gate electrode 401, a source electrode 402, a drain electrode 403, and an insulating film 404. The insulating film 404 can function as a gate insulating film in the TFT 111. The photoelectric conversion element 120 is arranged on an interlayer insulating film 406 formed on a protective film 405 formed on the TFT 111. The photoelectric conversion element 120 includes a structure in which a first impurity semiconductor layer 412, an intrinsic semiconductor layer 413, and a conductive second impurity semiconductor layer 414 opposite to the impurity semiconductor layer 412 are stacked in this order in between a lower electrode 411 and an upper electrode 415. The impurity semiconductor layer 412, the intrinsic semiconductor layer 413, and the impurity semiconductor layer 414 form a PIN photodiode, and photoelectric conversion is performed by this arrangement. Although a PIN photodiode is used as the photoelectric conversion element in this embodiment, an MIS element may be used as well. In addition, the power supply wiring line 114 is arranged on an interlayer insulating film 408 formed on a protective film 407 formed on the photoelectric conversion element 120. The upper portion of the pixel 102 is covered by a protective film 409. The power supply wiring line 114 is connected to the upper electrode 415 of the photoelectric conversion element 120 via a contact plug. The lower electrode 411 of the photoelectric conversion element 120 is connected to the drain electrode 403 of the TFT 111. Charges generated in the photoelectric conversion element 120 by photoelectric conversion are output from the source electrode 402 to the image signal line 112 when the TFT 111 is turned on by the gate electrode 401 connected to the image control wiring line 113.

FIG. 5 is an equivalent circuit diagram showing the circuit arrangement of the radiation imaging apparatus 100 according to this embodiment and shows a modification of the circuit arrangement shown in FIGS. 1 and 2. It is different from the equivalent circuit diagrams shown in FIGS. 1 and 2 in that instead of the detecting element 101 and the correction element 108, a pixel 131 in which a detecting element and an image pixel are paired and a pixel 132 in which a correcting element and an image pixel are paired have been arranged. The rest of the arrangement can be same as those shown in the radiation imaging apparatus 100 in FIGS. 1 and 2. By arranging an image conversion element in the region where the conversion element for detecting radiation has been arranged, pixel loss can be suppressed and image correction can be easily performed.

FIGS. 6A and 6B show plan views of the pixel 131 and the pixel 132, respectively, shown in FIG. 5. FIG. 6A shows a plan view of the pixel 131. The upper side of the pixel 131 has the same arrangement as the pixel 110 and includes a photoelectric conversion element 120*a* which has a smaller area than the photoelectric conversion element 120 of the pixel 110. The lower side of the pixel 131 has the same arrangement as the detecting element 101 and has a photoelectric conversion element 115*a* which has a smaller area than the photoelectric conversion element 115 of the detecting element 101. FIG. 6B shows a plan view of the pixel 132. The upper side of the pixel 132 has the same arrangement as the pixel 110 and includes the photoelectric conversion element 120*a* which has a smaller area than the photoelectric conversion element 120 of the pixel 110. The lower side of the pixel 132 has the same arrangement as the correction element 108 and includes a photoelectric conversion element 123*a* which has a smaller area than the photoelectric conversion element 123 of the correction element 108. Although the area of the photoelectric conversion element 120*a* is about ½ of the photoelectric conversion element 120 of each pixel 102 or 110, the same amount of output as each pixel 102 or 110 can be obtained by image processing such as offset correction and gain correction. In addition, the photoelectric conversion element 123*a* and the TFT 124 arranged in the pixel 132 can have the same structure as the photoelectric conversion element 115*a* and the TFT 119 arranged in the pixel 131. By making the conversion elements and the TFTs of the respective pixels 131 and 132 have the same structure, it becomes possible to correct the offset level and the dark current output from the conversion elements and the TFTs and change particularly due to the temperature. As a result, by subtracting the value of the electrical signal obtained from the correction signal line 103 from the value of the electrical signal obtained from detection signal line 104, radiation irradiation information of radiation irradiating the detecting element 101 can be accurately generated from the difference and obtained.

FIG. 7 is a schematic layout showing the radiation imaging apparatus 100 of this embodiment. The equivalent circuit diagrams shown in FIGS. 1, 2, and 5 are diagrams representing a partial region of the radiation imaging apparatus as described above. For example, FIG. 7 is a schematic layout view representing the entire radiation imaging apparatus 100, and 9 regions (3 rows×3 columns) have been provided in the pixel area including the equivalent circuit shown in FIG. 1. Pieces of information about the radiation that irradiates each pixel area can be collected by the readout circuit 170 and the information processing circuit 180 of the signal processing circuit 171. Although FIG. 1 showed an example in which one detecting element 101 and one correction element 108 were provided in a pixel area, three detecting elements 101 and three correction elements 108 are arranged in a pixel area in FIG. 7. The number of the detecting elements 101 to be connected to one detection signal line 104 may be the same as the number of correction elements 108 to be connected to one correction signal line 103. The sum of the pixels 110, the detecting elements 101, and the correction elements 108 that one detection signal line 104 runs through, can be the same as the sum of the pixels 110, the detecting elements 101, and the correction elements 108 that one correction signal line 103 runs through. By making numbers such as the number of detecting elements 101 and the correction elements 108 to be connected and the number of pixels 110, the detecting element 101, and the correction element 108 be equal, the radiation irradiation information of the irradiated detecting element 101 can be accurately obtained. In addition, for example, in the same manner as a pixel area E, the detecting elements 101 and the correction elements 108 can be arranged away from the edges of the image sensing region to be in the center of the image sensing region. The arrangement of the detecting elements 101 and correction elements 108 can be appropriately decided by the size and the arrangement of the object as the image sensing target.

The three detecting elements 101 in each pixel area are connected to a common detection signal line 104 and the three correction element 108 are connected to a common correction signal line 103. The columns of the respective detection signal lines 104 and the correction signal lines 103 are arranged by shifting their respective positions so they will not be shared by different pixel areas. By this arrangement, for example, when the detection control wiring lines 116 are driven to transfer signals from the detecting elements 101 and the correction elements 108 to the signal processing circuit 171, it is possible to simultaneously operate all of the detection control wiring lines 116. Compared to a case in which a readout operation is performed while scanning, a simultaneous readout operation can shorten the interval for reading out signals to obtain the radiation irradiation information and improves the readout speed. If the readout speed need not be improved, the detection signal line 104 and the correction signal line 103 can be made common in between the pixel areas in the vertical direction shown in FIG. 7 and the detection control wiring lines 116 are driven separately. This can simplify the processing circuit of the readout circuit 170 and decrease the number of terminals which are connected to the readout circuit 170.

FIG. 8 is a view showing the schematic layout of the radiation imaging apparatus 100 according to this embodiment and shows a modification of the schematic layout shown in FIG. 7. The layout of FIG. 8 is different from the layout shown in FIG. 7 in that the detection control wiring lines 116 are bundled together for each pixel area before being connected to the gate driving circuit 160. By this arrangement, the gate driving circuit 160 can be simplified and the number of terminals which are connected to the gate driving circuit 160 can be decreased.

FIG. 9 is a flowchart showing the sequence of the radiation imaging apparatus 100 according to this embodiment from the detection of radiation irradiation till determination of the irradiation intensity and output of the irradiation stop time. In step 901, the radiation imaging apparatus 100 maintains a standby state. When radiation irradiation is started, the process advances to step 902. In step 902, electrical signals transferred by the detection signal line 104 and the correction signal line 103 are sampled, and a difference is extracted in step 903. In step 904, the signal processing circuit 171 determines whether the radiation irradiation dose has stabilized based on the difference. If it is determined that the radiation irradiation dose has not stabilized, the process returns to step 902. Otherwise, the process advances to step 905. In step 905, the signal processing circuit 171 calculates the time (irradiation stop time)

to stop radiation irradiation based on the difference. The calculated irradiation stop time is transmitted in step 906 from the signal processing circuit 171 to a controller that controls the radiation source. The controller stops radiation irradiation based on this irradiation stop time. In this embodiment, control of radiation source is performed by the signal processing circuit 171 of the radiation imaging apparatus 100, but the present invention is not limited to this. Instead of calculating and outputting the irradiation stop time, radiation information for monitoring can be output from the radiation imaging apparatus 100 and the determination to stop the irradiation can be made by a control circuit which controls a tube for radiation irradiation.

A radiation imaging apparatus according to a second embodiment will be described with reference to FIGS. 10 to 12. FIG. 10 is an equivalent circuit diagram showing the circuit arrangement of a radiation imaging apparatus 100 according to this embodiment. Compared to the circuit arrangement shown in the first embodiment, it is different in that a detecting element 1001 and a correction element 1008 are directly connected to respective signal lines without going through a TFT serving as a switch element. In addition, the detection signal line and the correction signal line to which signals are respectively output from the detecting element 1001 and the correction element 1008 are configured by multi-purpose signal lines 1012 also serving as the respective image signal lines that output signals from the conversion elements of respective pixels 102. The rest of the arrangement can be the same as in the first embodiment.

As shown in FIG. 10, in the circuit arrangement of the radiation imaging apparatus 100 according to this embodiment, the detecting element 1001 and the correction element 1008 are directly connected to the multi-purpose signal line 1012 without going through a switch element such as a TFT or the like. In this embodiment, the size of the conversion element to be connected to the multi-purpose signal line 1012 of the correction element 1008 and the number of correction elements 1008 to be connected to the corresponding multi-purpose signal line 1012 are the same as those of the detecting elements 1001 to be connected to the corresponding multi-purpose signal line 1012. Meanwhile, in the same manner as the first embodiment, the size of the radiation detection region of the detecting element 1001 and that of the correction element 1008 are different. In this embodiment, the radiation detection region of the detecting element 1001 is formed larger than that of the correction element 1008. For example, in the case of a radiation imaging apparatus that directly converts radiation into electrical signals, for example, a heavy metal shielding member can be formed on the conversion element of the correction element 1008 as the shielding member to shield radiation. In the case of an indirect-type radiation imaging apparatus that uses a scintillator to convert radiation into light and converts this light into electrical signals, for example, an aluminum shielding film or the like can be provided on the conversion element of the correction element 1008 as the shielding member to shield light. Accordingly, in the same manner as in the first embodiment, information related to radiation irradiating the detecting element 1001 can be accurately generated by subtracting each signal output from the signal line to which the correction element 1008 is connected from each signal output from the signal line to which the detecting element 1001 is connected. Also, by directly connecting the conversion element to the signal line for transferring each signal output without going through a switch element to a signal processing circuit 171, control wiring lines for driving the detecting element 1001 and the correction element 1008 and switch elements such as a TFT or the like need not be arranged. Therefore, it becomes possible to simplify a gate driving circuit 160. In addition, the multi-purpose signal line 1012, which serves as the image signal line to which the conversion element of each pixel 102 is connected, is also used as the detection signal line and the correction signal line to which the detecting element 1001 and the correction element 1008 are respectively connected. As a result, the number of terminals which are connected to a readout circuit 170 can be decreased and the readout circuit 170 can be simplified.

In this manner, by using the detecting element 1001, the correction element 1008, and the multi-purpose signal line 1012, the circuit arrangement of this embodiment can simplify the structure and manufacturing process of the radiation imaging apparatus 100 compared to the circuit arrangement of the first embodiment.

FIG. 11 is an equivalent circuit diagram showing the circuit arrangement of the radiation imaging apparatus 100 according to this embodiment and shows a modification of the circuit arrangement shown in FIG. 10. This modification is different from the equivalent circuit diagram of the radiation imaging apparatus 100 shown in FIG. 10 in that the electrical signals output from the detecting element 1001 and the correction element 1008 are respectively input to a designated detection signal line 104 and a correction signal line 103 by the signal processing circuit 171 as shown in the first embodiment. The rest of the arrangement can be the same as in the radiation imaging apparatus 100 shown in FIG. 10. By this arrangement, the number of elements which are to be connected to an image signal line 112 can be decreased and reduce the capacitance of the image signal line 112. Therefore, it can provide a radiation imaging apparatus with a high signal to noise ratio (SNR).

FIGS. 12A and 12C show a plan view and a sectional view, respectively, of the detecting element 1001 and FIG. 12B shows a plan view of the correction element 1008. FIG. 12A is a plan view of the detecting element 1001. A photoelectric conversion element 115 is directly connected to the detection signal line 104 without providing a switch element such as a TFT. FIG. 12B is a plan view of the correction element 1008. In the correction element 1008, as in the same manner as in the detecting element 1001, a photoelectric conversion element 123 is also directly connected to the correction signal line 103 without going through a switch element. In addition, by providing a shielding member 122 between the correction element 1008 and the scintillator arranged above the image sensing region, the amount of light entering the photoelectric conversion element 123 is reduced. Hence, the sensitivity for changing radiation into an electrical signal will be different from that of the detecting element 1001, and the correction element 1008 can function as an element to correct the offset level or the dark current that changes due to the temperature at the time of driving. FIG. 12C is shows a sectional view taken along a line B-B' of the detecting element 1001 shown in FIG. 12A. Compared to the sectional view of the pixel 102 shown in FIG. 4, no TFT serving as a switch element is present. A lower electrode 411 of the photoelectric conversion element 115 and the detection signal line 104 are directly connected.

Although the two embodiments of the present invention has been described, the above-described embodiments can be appropriately changed and combined. Details concerning matters of design which are considered to be easily conceivable by a person skilled in the art are not described, and the present invention is not limited to the embodiments. For example, the conversion element, the scintillator, and the TFT can be made from different materials or arrangements, or a conversion element for directly detecting radiation may be used. In addition, the correction element 108 shown in FIG. 3D and the pixel 132 shown in FIG. 6B have arrangements in which the entire surfaces of the photoelectric conversion elements 123 and 123a are shielded, respectively. However, between the detecting element 101 and the correction element 108 or between the pixels 131 and 132, it is only necessary to have a conversion sensitivity difference between the radiation and the electrical signal, and for example, an opening that allows light to partially reach the conversion element can be provided on each of the photoelectric conversion elements 123 and 123a. Also, for example, one of the detection signal line 104 and the correction signal line 103, to which signals are respectively output from the detecting elements 101 and 1001 and the correction elements 108 and 1008, can be the multi-purpose signal line 1012 that also serves as the image signal line to which a signal from the conversion element of each pixel 102 is output.

A radiation imaging system incorporating the radiation imaging apparatus 100 according to the present invention will be exemplified with reference to FIG. 13. X-rays 6060 generated by an X-ray tube 6050 serving as a radiation source pass through a chest 6062 of a patient or object 6061 and enter the radiation imaging apparatus 100 according to the present invention. The incident X-rays include information about the inside of the body of the patient or object 6061. In the radiation imaging apparatus 100, a scintillator emits light in accordance with the entrance of the X-rays 6060, and the emitted light is photoelectrically converted by photoelectric conversion elements to obtain electrical information. This information is converted into digital data, undergoes image processing by an image processor 6070 serving as a signal processing unit, and can be observed on a display 6080 serving as a display unit in a control room. Also, this information can be transferred to a remote place by a transmission processing unit such as a telephone line 6090. This allows the information to be displayed on a display 6081 serving as a display unit in a doctor room or the like at another place, and even a doctor at the remote place can make a diagnosis. In addition, the information can be saved on a recording medium such as an optical disk and a film processor 6100 can also record the information on a film 6110 serving as a recording medium.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-104912, filed May 22, 2015, which is hereby incorporated by reference wherein in its entirety.

The invention claimed is:

1. A radiation imaging apparatus comprising:
a plurality of pixels arranged in an array in an image sensing region and configured to obtain a radiation image corresponding to a radiation irradiation dose;
at least one first detecting element and at least one second detecting element each including a conversion element configured to convert radiation into an electrical signal;
the first detecting element and the second detecting element configured to obtain radiation irradiation information corresponding to radiation irradiated to the radiation imaging apparatus, including at least one of start of radiation irradiation, end of radiation irradiation, a radiation irradiation intensity, or a radiation irradiation dose;
a first signal line to which an electrical signal from the first detecting element is configured to be output and a second signal line to which an electrical signal from the second detecting element is configured to be output; and
a signal processing circuit configured to process the electrical signal output from the first detecting element via the first signal line and the electrical signal output from the second detecting element via the second signal line, wherein
the radiation irradiation information is information different from the radiation image,
the first signal line and the second signal line are arranged in the image sensing region or arranged adjacent to the image sensing region,
a sensitivity of the second detecting element to convert radiation into an electrical signal is lower than that of the first detecting element, and
the signal processing circuit generates the radiation irradiation information based on a difference between the electrical signal from the first signal line and the electrical signal from the second signal line.

2. The apparatus according to claim 1, wherein a region to detect radiation of the first detecting element is larger than that of the second detecting element, the first detecting element and the second detecting element are arranged in the image sensing region.

3. The apparatus according to claim 1, further comprising a scintillator configured to convert radiation into light,
the conversion element is configured to convert the light into the electrical signal, and
the second detecting element includes, between the scintillator and the conversion element of the second detecting element, a shielding member that shields the light.

4. The apparatus according to claim 1, wherein the conversion element of the first detecting element and the conversion element of the second detecting element have the same structure.

5. The apparatus according to claim 1, wherein the first detecting element includes a first switch element between the conversion element of the first detecting element and the first signal line, and
the second detecting element includes a second switch element between the conversion element of the second detecting element and the second signal line.

6. The apparatus according to claim 5, wherein the first switch element and the second switch element have the same structure.

7. The apparatus according to claim 1, wherein the conversion element of the first detecting element and the first signal line are directly connected, and
the conversion element of the second detecting element and the second signal line are directly connected.

8. The apparatus according to claim 1, wherein the number of the first detecting elements to be connected to the first signal line is equal to the number of the second detecting elements to be connected to the second signal line.

9. The apparatus according to claim 1, wherein the first signal line and the second signal line each include a region that overlaps a part of the plurality of pixels, the first detecting element and the second detecting element in planar view with respect to the image sensing region, and a sum of the number of pixels in the plurality of pixels that overlap the first signal line, the numbers of first detecting elements that overlap the first signal line, and the numbers of second detecting elements that overlap the first signal line is equal to a sum of the number of pixels the plurality of pixels that overlap the second signal line, the numbers of first detecting elements that overlap the second signal line, and the numbers of second detecting elements that overlap the second signal line.

10. The apparatus according to claim 1, further comprising a plurality of image signal lines to which electrical signals from the plurality of pixels are to configured to be output, and
at least one image signal line out of the plurality of image signal lines also serves as the first signal line or the second signal line.

11. The apparatus according to claim 1, further comprising a plurality of image signal lines to which electrical signals from the plurality of pixels are configured to be output.

12. The apparatus according to claim 1, wherein the signal processing circuit controls a radiation source by using the radiation irradiation information.

13. A radiation imaging system, comprising:
a radiation imaging apparatus according to claim 1; and
a signal processing unit configured to process a signal from the radiation imaging apparatus.

14. A radiation imaging apparatus, comprising:
a plurality of pixels arranged in an array in an image sensing region and configured to obtain a radiation image;
a first detecting element and a second detecting element each including a conversion element configured to convert radiation into an electrical signal, being for obtaining radiation irradiation information, corresponding to radiation irradiated to the image sensing region, including at least one of start of radiation irradiation, end of radiation irradiation, a radiation irradiation intensity, or a radiation irradiation dose;
a signal processing circuit configured to process a first electrical signal output from the first detecting element and a second electrical signal output from the second detecting element, wherein
the radiation irradiation information is information different from the radiation image,
a sensitivity of the second detecting element to convert radiation into an electrical signal is lower than that of the first detecting element, and
the signal processing circuit generates the radiation irradiation information based on a difference between the first electrical signal and the second electrical signal.

15. The apparatus according to claim 14, wherein the first detecting element and the second detecting element are arranged in the image sensing region.

16. The apparatus according to claim 14, further comprising a scintillator configured to convert radiation into light,
the conversion element is configured to convert the light into the electrical signal, and
the second detecting element includes, between the scintillator and the conversion element of the second detecting element, a shielding member that is configured to shield the light such that a region for detecting the radiation is smaller than the first detection element to cause the sensitivity of the second detecting element to convert radiation into an electrical signal is lower than that of the first detecting element.

17. The apparatus according to claim 14, wherein the conversion element of the first detecting element and the conversion element of the second detecting element have the same structure.

18. The apparatus according to claim 14, wherein the first detecting element includes a first switch element between the conversion element of the first detecting element and a first signal line to which the first electrical signal from the first detecting element is to be output, and
the second detecting element includes a second switch element between the conversion element of the second detecting element and a second signal line to which the second electrical signal from the second detecting element is to be output.

19. The apparatus according to claim 18, wherein the first switch element and the second switch element have the same structure.

20. The apparatus according to claim 18, wherein the number of the first detecting elements to be connected to the first signal line is equal to the number of the second detecting elements to be connected to the second signal line.

21. The apparatus according to claim 18, wherein the first signal line and the second signal line each include a region that overlaps a part of the plurality of pixels, the first detecting elements and the second detecting elements in planar view with respect to the image sensing region, and
a sum of the number of pixels in the plurality of pixels that overlap the first signal line, the numbers of first detecting elements that overlap the first signal line, and the numbers of second detecting elements that overlap the first signal line is equal to a sum of the number of pixels in the plurality of pixels that overlap the second signal line, the numbers of first detecting elements that overlap the second signal line, and the numbers of second detecting elements that overlap the second signal line.

22. The apparatus according to claim 18, further comprising a plurality of image signal lines to which electrical signals from the plurality of pixels are to be output, and
at least one image signal line out of the plurality of image signal lines also serves as the first signal line or the second signal line.

23. The apparatus according to claim 18, further comprising a plurality of image signal lines to which electrical signals from the plurality of pixels are to be output.

24. The apparatus according to claim 14, wherein the conversion element of the first detecting element and a first signal line to which the first electrical signal from the first detecting element is to be output are directly connected, and
the conversion element of the second detecting element and a second signal line to which the second electrical signal from the second detecting element is to be output are directly connected.

25. The apparatus according to claim 14, wherein the signal processing circuit controls a radiation source by using the radiation irradiation information.

26. A radiation imaging system, comprising:
a radiation imaging apparatus according to claim 14; and
a signal processing unit configured to process a signal from the radiation imaging apparatus.

27. A radiation imaging apparatus, comprising:
a plurality of pixels arranged in an array in an image sensing region and configured to convert light converted from radiation by a scintillator into an electrical signal to obtain a radiation image;
a first photoelectric conversion element and a second photoelectric conversion element configured to convert light converted by the scintillator into an electrical signal, being for obtaining radiation irradiation information, corresponding to radiation irradiated to the image sensing region, including at least one of start of radiation irradiation, end of radiation irradiation, a radiation irradiation intensity, or a radiation irradiation dose;

a signal processing circuit configured to process a first electrical signal output from the first photoelectric conversion element and a second electrical signal output from the second photoelectric conversion element, wherein the radiation irradiation information is information different from the radiation image, a region of the second photoelectric conversion element for detecting the radiation is smaller than that of the first detection element by a shielding member that is arranged between the scintillator and the second photoelectric conversion element and shields the light converted by the scintillator, and a sensitivity of the second photoelectric conversion element to convert radiation into an electrical signal is lower than that of the first photoelectric conversion element, and the signal processing circuit generates the radiation irradiation information based on a difference between the first electrical signal and the second electrical signal.

28. A radiation imaging system, comprising:

a radiation imaging apparatus according to claim 27; and a signal processing unit configured to process a signal from the radiation imaging apparatus.

* * * * *